United States Patent
Jang et al.

(10) Patent No.: US 9,658,364 B2
(45) Date of Patent: *May 23, 2017

(54) METHOD FOR STORING EPISULFIDE COMPOUND AND METHOD FOR PREPARING THIOEPOXY-BASED OPTICAL MATERIAL USING SAID EPISULFIDE COMPOUND

(71) Applicant: KOC SOLUTION CO., LTD., Daejeon (KR)

(72) Inventors: Dong Gyu Jang, Daejeon (KR); Soo Gyun Roh, Daejeon (KR); Jong Hyo Kim, Daejeon (KR); Bong-Keun So, Daejeon (KR); Jin-Moo Seo, Daejeon (KR)

(73) Assignee: KOC SOLUTION CO., LTD., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/430,802

(22) PCT Filed: Sep. 24, 2013

(86) PCT No.: PCT/KR2013/008549
§ 371 (c)(1),
(2) Date: Mar. 24, 2015

(87) PCT Pub. No.: WO2014/046523
PCT Pub. Date: Mar. 27, 2014

(65) Prior Publication Data
US 2015/0247955 A1  Sep. 3, 2015

(30) Foreign Application Priority Data

Sep. 24, 2012 (KR) ........................ 10-2012-0105853

(51) Int. Cl.
*C08G 75/06* (2006.01)
*C08L 81/02* (2006.01)
*G02B 1/04* (2006.01)
*C08G 75/02* (2016.01)
*C07D 331/02* (2006.01)
*G02B 1/08* (2006.01)

(52) U.S. Cl.
CPC ........... *G02B 1/041* (2013.01); *C07D 331/02* (2013.01); *C08G 75/02* (2013.01); *C08L 81/02* (2013.01); *G02B 1/08* (2013.01); *G02B 1/04* (2013.01)

(58) Field of Classification Search
None
See application file for complete search history.

(56) References Cited

U.S. PATENT DOCUMENTS 9,372,281 B2 *  6/2016  Jang ............... C07D 409/12
2003/0171533 A1 *  9/2003  Tamura ............... C08G 75/08
                                                          528/377
2005/0124783 A1    6/2005  Morijiri et al.

FOREIGN PATENT DOCUMENTS

| JP | 11-352302 | | 12/1999 | | |
|---|---|---|---|---|---|
| JP | 11-352302 | A * | 12/1999 | | |
| JP | 2000-256463 | A | 9/2000 | | |
| KR | 10-1992-0005708 | B | 7/1992 | | |
| KR | 10-1993-0006918 | B | 7/1993 | | |
| KR | 10-0417985 | | 2/2004 | | |
| KR | 10-2006-0105051 | A | 10/2006 | | |
| KR | 10-0681218 | | 2/2007 | | |
| KR | 10-0681218 | B1 * | 2/2007 | ............ | C08G 65/22 |
| KR | 10-2008-0053958 | A | 6/2008 | | |
| KR | WO 2013/089538 | A1 * | 6/2013 | .......... | C08G 59/302 |
| KR | WO 2013/109119 | A1 * | 7/2013 | ............... | G02B 1/04 |

OTHER PUBLICATIONS

Abstract for Korean Patent No. 10-0417985 B1, Feb. 14, 2004, one page.*
Metrohm, 860 KF Thermoprep Manual, 64 pages, Jul. 2011, Switzerland.†
API Corporation, p. 146 of Karl-Fischer Reagents Manual (in Japanese, with English translation), 1 page, Jun. 27, 2013, Japan.†
Certificate of Experimental Results (in Japanese, with English translation), 2 pages, May 2015, publicly available from and obtained by written request to the Korean Patent Office (also included are Korean version of Certificate of Experimental Results (4 pages), all of which (with the exception of the English translation) were obtained by written request to the Korean Patent Office (2 pages) attached).†

\* cited by examiner
† cited by third party

*Primary Examiner* — Robert Sellers
(74) *Attorney, Agent, or Firm* — Susan Paik, Esq.

(57) ABSTRACT

Disclosed is a method of storing a thioepoxy compound and a method of preparing a thioepoxy based optical material using the thioepoxy compound. Particularly, a method of preparing a high-quality thioepoxy based optical material having superior color and thermal stability and less time-dependent change, and being colorless and transparent by inhibiting time-dependent change of the thioepoxy compound during storage is disclosed. In addition, a method of storing the thioepoxy compound for an optical material, the thioepoxy compound having a water content of 500 to 2,500 ppm and stored at −78 to 10° C., and a method of preparing the thioepoxy based optical material, the method including polymerizing a polymerizable composition including the stored thioepoxy compound, are provided. The high-quality thioepoxy based optical material, which is colorless and transparent, prepared according to the present invention may be broadly used in a variety of fields as a substitute for conventional optical materials.

12 Claims, No Drawings

METHOD FOR STORING EPISULFIDE COMPOUND AND METHOD FOR PREPARING THIOEPOXY-BASED OPTICAL MATERIAL USING SAID EPISULFIDE COMPOUND

TECHNICAL FIELD

The present invention relates a method of storing an polyepisulfide compound and a method of preparing a polythioepoxy based optical material using the same. More particularly, the present invention relates to an polyepisulfide compound having superior color and thermal stability by inhibiting time-dependent change during storage, and a method of preparing a high-quality polythioepoxy based optical material exhibiting less time-dependent change and being colorless and transparent using the polyepisulfide compound.

BACKGROUND ART

Plastic optical lenses were introduced as alternatives to glass lenses having problems such as a high specific gravity and low impact resistance. As representative examples, there are polyethylene glycol bis(allyl carbonate), polymethylmethacrylate, diallyl phthalate, and the like. Although optical lenses prepared from the polymers exhibit superior properties such as moldability, dyeability, adhesive properties of hard coated films, impact resistance, and the like, lenses are thickened due to a low refractive index of approximately 1.50 (nD) and 1.55 (nD). Accordingly, in order to reduce the thicknesses of lenses, a variety of attempts have been made to develop an optical material having a high refractive index.

Korean Application Pub. Nos. 1993-0006918 and 1992-0005708 suggest a thiourethane based lens in which a polythiol compound and a polyisocyanate compound are reacted. In addition, Korean Patent No. 10-0681218 suggests a polythioepoxy based plastic lens. The thiourethane based lens, one of existing lenses, has advantages such as a high refractive index and superior impact strength. However, the thiourethane based lens has drawbacks such as a soft surface, a dented center, and the like. In addition, the thiourethane based lens has a problem such as rapidly reduced Abbe's number with increasing refractive index. The polythioepoxy based lens has properties such as a high refractive index and a high Abbe's number. However, the polythioepoxy based lens is fragile and dying thereof is not easy. To resolve the problems, a method of copolymerizing two resin types having different properties, namely, a method of copolymerizing a polythioepoxy compound, a polythiol compound, and a polyisocyanate compound, was suggested in Korean Patent No. 10-0417985, Japanese Application Pub. No. hei 11-352302, and the like.

However, in the cases of the polythioepoxy based lens, or the lens in which polythioepoxy and thiourethane are copolymerized, an undesired coloring phenomenon reducing transparency and thermal strain due to exposure to high temperature may be exhibited. Since such a coloring phenomenon and thermal strain deteriorate lens quality, there is a need for quality improvement.

PRIOR ART LITERATURE

Patent Literature (Patent Literature 1) Korean Patent No. 10-0681218
(Patent Literature 2) Korean Patent No. 10-0417985
(Patent Literature 3) Japanese Application Pub. No. hei 11-352302

SUMMARY OF THE INVENTION

Technical Problem

The present inventor tried to improve a coloring phenomenon, which reduces transparency, and thermal stability, which are exhibited in a polythioepoxy based lens or a lens in which polythioepoxy and thiourethane are copolymerized. In the meantime, the inventors confirmed that time-dependent change of a polythioepoxy compound used as a monomer directly affects color, transparency, and thermal stability of lenses. Transparency reduction of the polythioepoxy based lens or the lens copolymerized with thiourethane was related to uncontrolled polymerization rate and thermal stability of the lenses was related to polymerization imbalance. In addition, time-dependent change of the polythioepoxy compound directly affects polymerization rate control and polymerization imbalance and, as such, transparency of polymerized lenses and thermal stability are deteriorated. Furthermore, the inventors confirmed that the time-dependent change of the polythioepoxy compound is directly affected by storage temperature and a water content of the polythioepoxy compound. When a lens was polymerized using the polythioepoxy compound after storing the polythioepoxy compound while controlling a water content and storage temperature at the same time to maximally inhibit time-dependent change, a high-quality optical material having superior color and thermal stability and less time-dependent change, and being colorless and transparent was prepared. The present inventors confirmed and completed the above particulars.

Therefore, the present invention has been made in view of the above problems, and it is an object of the present invention to provide a storage method to inhibit time-dependent change of the polythioepoxy compound and a method of preparing a polythioepoxy based optical material using the polythioepoxy compound stored according to the storage method.

Technical Solution

In the present invention, "polythioepoxy compound" is defined as a compound having one polythioepoxy group or thiirane group, or more in a molecular structure of the compound.

In the present invention, "polythioepoxy based optical material" is defined as an optical material obtained by polymerizing a polymerizable composition including the polythioepoxy compound. In particular, "polythioepoxy based optical material" includes an optical material in which the polythioepoxy compound is polymerized and an optical material in which the polythioepoxy compound, a polythiol compound, and a polyisocyanate compound are copolymerized.

In accordance with an aspect of the present invention, the above and other objects can be accomplished by the provision of a method of storing a polythioepoxy compound for an optical material, the method including storing a polythioepoxy compound having a water content of 500 to 2,500 ppm at −78 to 10° C.

In accordance with another aspect of the present invention, there are provided a method of preparing a polythioepoxy based optical material, the method including polymerizing a polymerizable composition Including a polythioepoxy compound having a water content of 500 to 2,500 ppm, stored at −78 to 10° C.

In accordance with yet another aspect of the present invention, there are provided a polythioepoxy based optical material obtained according to the method and an optical lens composed of the polythioepoxy based optical material. The optical lens particularly includes eyeglass lenses or polarizing lenses.

Advantageous Effects

As described above, a high-quality optical material having superior color and thermal stability and less time-dependent change, and being colorless and transparent may be prepared by inhibiting time-dependent change of a polythioepoxy compound during storage.

DETAILED DESCRIPTION OF PREFERRED EMBODIMENTS

The present invention maximally inhibits time-dependent change by storing a polythioepoxy compound having a water content of 500 to 2,500 ppm at −78 to 10° C.

When a polythioepoxy compound containing water of a constant range was stored at a low temperature of 10° C. or less, environmental influence inducing time-dependent change was maximally excluded. Preferably, the prepared polythioepoxy compound is stored at −50 to 0° C. From an economic point of view, the storage temperature is most preferably −30 to −10° C.

Time-dependent change of the polythioepoxy compound is affected, in addition to temperature, by water content. A range of the water content is preferably 500 to 2,500 ppm. Reactivity of the polythioepoxy compound is inhibited by the presence of water. When water existed to the range, storage stability was most effective. When water content in the polythioepoxy compound stored was greater than 2,500 ppm, undesired time-dependent change was exhibited even in the temperature range. On the other hand, when a water content in the polythioepoxy compound stored was less than 500 ppm, reactivity of the polythioepoxy compound increased during storage and, as such, time-dependent change representing color occurred. More preferably, the water content range is 600 to 1,500 ppm. The water content of the polythioepoxy compound may be accomplished by controlling a preparation condition, supplementing water when a measured water content of the polythioepoxy compound is low, and removing water when a measured water content of the polythioepoxy compound is high. Preferably, water may be removed separately or parallely using a method of defoaming under vacuum, a method of removing water with a compound such as $MgSO_4$, $Na_2SO_4$, $CaCl_2$, or $CaSO_4$, or the like. In addition, all publicly known methods used to remove water may be used.

When the polythioepoxy compound having the water content is stored at the temperature range, storage stability of the polythioepoxy compound may be maintained for long time. A storage period of the polythioepoxy compound is preferably 3 years or less, more preferably 2 years or less.

When an optical material is prepared by polymerizing a polymerizable composition prepared using the polythioepoxy compound stored as described above, a polythioepoxy based optical material having superior color and thermal stability and less time-dependent change, and being colorless and transparent may be obtained.

The polythioepoxy compound may be at least type of an polyepisulfide compound having a cycloaliphatic backbone such as bis(2,3-epithiopropyl)sulfide, bis(2,3-epithiopropyl)disulfide, 1,3-bis(β-epithiopropylthio)cyclohexane(=1,3-(bis(2,3--epithiopropylthio))cyclohexane), 1,4-bis(β-epithiopropylthio)cyclohexane(=1,4-(bis(2,3-epithiopropylthio))cyclohexane), 1,3-bis(β-epithiopropylthiomethyl)cyclohexane(=1,3-(bis(2,3-epithiopropylthiomethyl))cyclohexane), 1,4-bis(β-epithiopropylthiomethyl)cyclohexane(=1,4-(bis(2,3-epithiopropylthiomethyl))cyclohexane), bis[4-β-epithiopropylthio)cyclohexyl]methane, 2,2-bis[4-(β-epithiopropylthio)cyclohexyl]propane, bis[4-(β-epithiopropylthio)cyclohexyl]sulfide, or the like; an polyepisulfide compound having a dithiane chain backbone such as an polyepisulfide compound having an aromatic backbone such as 1,3-bis(β-epithiopropylthiomethyl)benzene, 1,4-bis(β-epithiopropylthiomethyl)benzene, bis[4-β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]disulfide, bis[4-(β-epithiopropylthio)phenyl]sulfin, 4,4-bis(β-epithiopropylthio)biphenyl, or the like; an polyepisulfide compound having an aliphatic backbone such as 2,5-bis(β-epithiopropylthiomethyl)-1,4-dithiane, 2,5-bis(β-epithiopropylthioethylthiomethyl)-1,4-dithiane, 2,5-bis(β-epithiopropylthioethyl)-1,4-dithiane, 2,3,5-tri(β-epithiopropylthioethyl)-1,4-dithiane, or the like; 2-(2-β-epithiopropylthioethylthio)-1,3-bis(β-epithiopropylthio)propane, 1,2-bis[(2-β-epithiopropylthioethyl)thio]-3-(β-epithiopropylthio)propane, tetrakis(β-epithiopropylthiomethyl)methane, 1,1,1-tris(β-epithiopropylthiomethyl)propane, bis-(β-epithiopropyl)sulfide, bis-(β-epithiopropyl)disulfide, or the like; and the like. In addition, a chlorine substituent of a compound having an polyepisulfide group, a halogen substituent such as a bromine substituent or the like, an alkyl substituent, an alkoxy substituent, a nitro substituent, or a prepolymer-typed polymer modified with polythiol may be used as the polythioepoxy compound. As the polythioepoxy group compound, at least one of bis(2,3-epithiopropyl)sulfide, bis(2,3-epithiopropyl)disulfide, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, 2,5-bis(β-epithiopropylthiomethyl)-1,4-dithiane, 2,5-bis(β-epithiopropylthioethylthiomethyl)-1,4-dithiane, 2-(2-β-epithiopropylthioethylthio)-1,3-bis(β-epithiopropylthio)propane is preferably used.

The polymerizable composition may further include a polyisocyanate compound and/or a polythiol compound.

The polyisocyanate compound of the present invention is not specifically limited and may be a compound having at least one isocyanate group and/or isothiocyanate group. For example, one or a mixture of two or more of an aliphatic isocyanate compound such as 2,2-dimethylpentane diisocyanate, 2,2,4-trimethylhexane diisocyanate, hexamethylene diisocyanate, pentamethylene diisocyanate, butene diisocyanate, 1,3-butadiene-1,4-diisocyanate, 2,4,4-trimethyl hexamethylene diisocyanate, 1,6,11-undeca triisocyanate, 1,3,6-hexamethylene triisocyanate, 1,8-diisocyanate-4-isocyanate methyl octane, bis(isocyanate ethyl)carbonate, bis(isocyanate ethyl)ether, 3,8-bis(isocyanate methyl)tricyclo[5,2,1,02,6]decane, 3,9-bis(isocyanate methyl)tricyclo[5,2,1,02,6]decane, 4,8-bis(isocyanate methyl)tricyclo[5,2,1,02,6]decane, 4,9-bis(isocyanate methyl)tricyclo[5,2,1,02,6]decane, 2,5-bis(isocyanate methyl)bicyclo[2,2,1]heptane, 2,6-bis(isocyanate methyl)bicyclo[2,2,1]heptane, or the like; a cycloaliphatic isocyanate compound such as isophorone diisocyanate, 1,2-bis(isocyanate methyl)cyclohexane, 1,3-bis(isocyanate methyl)cyclohexane, 1,4-bis(isocyanate methyl)cyclohexane, dicyclohexylmethane diisocyanate, cyclohexane diisocyanate, methylcyclohexane diisocyanate, dicyclohexyl dimethylmethane isocyanate, 2,2-dimethyl dicyclohexylmethane isocyanate, or the like; an aromatic isocyanate compound such as bis(isocyanatoethyl)benzene, bis(isocyanatopropyl)benzene, bis(isocyanatobutyl)benzene, bis(isocyanatomethyl)naphthalene, bis(isocyanatomethyl)diphenylether, phenylene diisocyanate, ethylphenylene diisocyanate, isopropyl phenylene diisocyanate, dimethyl phenylene diisocyanate, diethyl phenylene diisocyanate, diisopropyl phenylene diisocyanate, trimethylbenzene triisocyanate, benzene triisocyanate, biphenyl diisocyanate, toluidine diisocyanate, 4,4-diphenylmethane diisocyanate, 3,3-dimethyl diphenylmethane-4,4-diisocyanate, bibenzyl-4,4-diisocyanate, bis(isocyanate phenyl)ethylene, 3,3-dimethoxybiphenyl-4,4-diisocyanate, hexahydro benzene diisocyanate, hexahydro diphenylmethane-4,4-diisocyanate, xylene diisocyanate, tolylene diisocyanate or the like; a sulfur-containing aliphatic isocyanate compound such as bis(isocyanatoethyl)sulfide, bis(isocyanatopropyl)sulfide, bis(isocyanatohexyl)sulfide, bis(isocyanatomethyl)sulfone, bis(isocyanatomethyl)disulfide, bis(isocyanatopropyl)disulfide, bis(isocyanatomethylthio)methane, bis(isocyanatoethylthio)methane, bis(isocyanatoethylthio)ethane, bis(isocyanatomethylthio)ethane, 1,5-diisocyanate-2-isocyanatomethyl-3-thiapentane, or the like; a sulfur-containing heterocyclic isocyanate compound such as a sulfur-containing aromatic isocyanate compound such as diphenylsulfide-2,4-diisocyanate, diphenylsulfide-4,4-diisocyanate, 3,3-dimethoxy-4,4-diisocyanatedibenzylthioether, bis(4-isocyanatomethylbenzene)sulfide, 4,4-methoxybenzenethioethylene glycol-3,3-diisocyanate, diphenyldisulfide-4,4-diisocyanate, 2,2-dimethyl diphenyl disulfide-5,5-diisocyanate, 3,3-dimethyl diphenyl disulfide-5,5-diisocyanate, 3,3-dimethyl diphenyl disulfide-6,6-diisocyanate, 4,4-dimethyl diphenyl disulfide-5,5-diisocyanate, 3,3-dimethoxy diphenyldi sulfide-4,4-diisocyanate, 4,4-dimethoxy diphenyl disulfide-3,3-diisocyanate, or the like; 2,5-diisocyanate thiophene, 2,5-bis(isocyanatomethyl)thiophene, 2,5-diisocyanate tetrahydrothiophene, 2,5-bis(isocyanatomethyl)tetrahydrothiophene, 3,4-bis(isocyanatomethyl)tetrahydrothiophene, 2,5-diisocyanate-1,4-dithiane, 2,5-bis(isocyanatomethyl)-1,4-dithiane, 4,5-diisocyanate-1,3-dithiolan, 4,5-bis(isocyanatomethyl)-1,3-dithiolan, 4,5-bis(isocyanatomethyl)-2-methyl-1,3-dithiolan, or the like; and the like may be used. In addition, a compound or more having at least one isocyanate and/or isothiocyanate group may be mixed. In addition, a chlorine substituent of the isocyanate compound, a halogen substituent such as a bromine substituent, an alkyl substituent, an alkoxy substituent, a nitro substituent, a prepolymer-typed polymer modified with polyhydric alcohol or thiol, modified carbodiimide, modified urea, modified biuret, a dimerized or trimerized reactive product, or the like may be used. As the polyisocyanate compound, at least one type selected from the group consisting of isophorone diisocyanate, hexamethylene diisocyanate, dicyclohexylmethane diisocyanate, bis(isocyanate methyl)tricyclo[5,2,1,02,6]decane, bis(isocyanate methyl)bicyclo[2,2,1]heptane, xylene diisocyanate, and tolylene diisocyanate is preferably used.

The polythiol compound is not specifically limited and may be one or a mixture of two or more of compounds having at least one thiol group. For example, the polythiol compound may be bis(2-mercaptoethyl)sulfide, 4-mercaptomethyl-1,8-dimercapto-3,6-dithiaoctane, 2,3-bis(2-mercaptoethylthio)propane-1-thiol, 2,2-bis(mercaptomethyl)-1,3-propanedithiol, tetrakis(mercaptomethyl)methane; 2-(2-mercaptoethylthio)propane-1,3-dithiol, 2-(2,3-bis(2-mercaptoethylthio)propylthio)ethanethiol, bis(2,3-dimercaptopropanyl)sulfide, bis(2,3-dimercaptopropanyl)disulfide, 1,2-bis(2-mercaptoethylthio)-3-mercaptopropane, 1,2-bis(2-(2-mercaptoethylthio)-3-mercaptopropylthio)ethane, bis(2-(2-mercaptoethylthio)-3-mercaptopropyl)sulfide, 2-(2-mercaptoethylthio)-3-2-mercapto-3-[3-mercapto-2-(2-mercaptoethylthio)-propylthio]propylthio-propane-1-thiol, 2,2-bis-(3-mercapto-propionyloxymethyl)-butyl ester, 2-(2-mercaptoethylthio)-3-(2-(2-[3-mercapto-2-(2-mercaptoethylthio)-propylthio]ethylthio)ethylthio)propane-1-thiol, (4R,11S)-4,11-bis(mercaptomethyl)-3,6,9,12-tetrathiatetradecane-1,14-dithiol, (S)-3-((R-2,3-dimercaptopropyl)thio)propane-1,2-dithiol, (4R,14R)-4,14-bis(mercaptomethyl)-3,6,9,12,15-pentathiaheptane-1,17-dithiol,(S)-3-((R-3-mercapto-2-((2-mercaptoethyl)thio)propyl)thio)propyl)thio)-2-((2-mercaptoethyl)thio)propane-1-thiol, 3,3'-dithiobis(propane-1,2-dithiol), (7R,11S)-7,11-bis(mercaptomethyl)-3,6,9,12,15-pentathiaheptadecane-1,17-dithiol, (7R,12S)-7,12-bis(mercaptomethyl)-3,6,9,10,13,16-hexathiaoctadecane-1,18-dithiol, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, pentaerythritol tetrakis(3-mercaptopropionate), trimethylolpropane tris(3-mercaptopropionate), pentaerythritol tetrakis(2-mercaptoacetate), bispentaerythritol-ether-hexakis(3-mercaptopropionate), 1,1,3,3-tetrakis(mercaptomethylthio)propane, 1,1,2,2-tetrakis(mercaptomethylthio)ethane, 4,6-bis(mercaptomethylthio)-1,3-dithiane, 2-(2,2-bis(mercaptodimethylthio)ethyl)-1,3-dithiane, or the like. In addition, one or a mixture of two or more of compounds having at least one thiol group may be used. Furthermore, a modified polymer obtained by prepolymerizing the polythiol compound with a compound having an unsaturated bond, such as an isocyanate or polythioepoxy compound, a thietane compound or a resin modifier may also be used. As the polythiol compound, a mixture of bis(2-mercaptoethyl)sulfide or bis(2-mercaptoethyl)sulfide and at least one different polythiol compound is preferably used.

The polymerizable composition may further include an olefin compound as a reactive resin modifier so as to improve optical properties of an optical resin copolymer (optical material) and, thus, control impact resistance, a specific gravity, viscosity of monomers, and the like. The olefin compound added as a reactive resin modifier may, for example, be a (meth)acrylate compound such as benzyl acrylate, benzyl methacrylate, butoxyethyl acrylate, butoxymethyl methacrylate, cyclohexyl acrylate, cyclohexyl methacrylate, 2-hydroxyethyl acrylate, 2-hydroxymethyl methacrylate, glycidyl acrylate, glycidylmethacrylate, phenoxy ethylacrylate, phenoxyethylmethacrylate, phenylmethacrylate, ethylene glycol diacrylate, ethylene glycol dimethacrylate, diethyleneglycol diacrylate, diethyleneglycol dimethacrylate, triethylene glycol diacrylate, triethylene glycol dimethacrylate, tetraethylene glycol diacrylate, tetraethylene glycol dimethacrylate, polyethylene glycol diacrylate, polyethylene glycol dimethacrylate, neopentylglycol diacrylate, neopentylglycol dimethacrylate, ethylene glycol bisglycidyl acrylate, ethylene glycolbisglycidylmethacrylate, bisphenol A diacrylate, bisphenol A dimethacrylate, 2,2-bis(4-acroxyethoxyphenyl)propane, 2,2-bis(4-methacroxyethoxyphenyl)propane, 2,2-bis(4-acroxydiethoxyphenyl)propane, 2,2-bis(4-methacroxydiethoxyphenyl)propane, bisphenol F diacrylate, bisphenol F dimethacrylate, 1,1-bis (4-acroxyethoxyphenyl)methane, 1,1-bis(4-methacroxyethoxyphenyl)methane, 1,1-bis(4-acroxydiethoxyphenyl)methane, 1,1-bis(4-methacroxydiethoxyphenyl)methane, dimethyloltricyclodecanediacrylate, trimethylolpropane triacrylate, trimethylolpropane trimethacrylate, glycerol diacrylate, glycerol dimethacrylate, pentaerythritol triacrylate, pentaerythritol tetracrylate, pentaerythritol tetramethacrylate, methylthioacrylate, methylthiomethacrylate, phenylthioacrylate, benzylthiomethacrylate, xylenedithiol diacrylate, xylenedithioldimethacrylate, mercaptoethylsulfide diacrylate, mercaptoethylsulfidedimethacrylate, or the like; or an allyl compound such as allylglycidylether, diallyl phthalate, diallylterephthalate, diallylisophthalate, diallylcarbonate, diethyleneglycol bis(allylcarbonate), or the like; and a vinyl compound such as styrene, chlorostyrene, methylstyrene, bromostyrene, dibromostyrene, divinylbenzene, 3,9-divinylspirobi(meta-dioxane), or the like, but a used compound is not limited thereto. The olefin compound may be used alone or as a mixture of two olefin compounds or more.

The polymerizable composition may further include a mold release agent, a thermal stabilizer, an ultraviolet ray absorbent, an organic dye, an inorganic dye, an anti-coloring agent, an antioxidant, a light stabilizer, a catalyst, and the like, according to general methods.

As the mold release agent, a phosphoric ester compound, a silicon based surfactant, a fluorine based surfactant, and the like may used alone or as a mixture of two or more thereof. The mold release agent is included in an amount of particularly 0.001 to 10 wt % in the polymerizable composition. As the mold release agent, a phosphoric ester compound is particularly used. The phosphoric ester compound is prepared by adding 2 to 3 mol of an alcohol compound to phosphorus pentoxide ($P_2O_5$). Here, a variety of phosphoric ester compounds may be obtained according to alcohol types. As representative examples, there are ethylene oxide or propylene oxide added to aliphatic alcohol, and ethylene oxide or propylene oxide added to a nonylphenol group or the like. When the phosphoric ester compound including the ethylene oxide or the propylene oxide as a mold release agent is added to the polymerizable composition of the present invention, a high-quality optical material having superior releasing properties may be desirably obtained. The phosphoric ester compound used as a mold release agent is one or more selected from the group consisting of particularly polyoxyethylene nonylphenol ether phosphate (in an amount of 5 wt % including 5 mol of ethylene oxide, 80 wt % including 4 mol of ethylene oxide, 10 wt % including 3 mol of ethylene oxide, or 5 wt % including 1 mol of ethylene oxide), polyoxyethylene nonylphenyl phosphate (in an amount of 5 wt % including 9 mol of ethylene oxide, 80 wt % including 8 mol of ethylene oxide, 10 wt % including 7 mol of ethylene oxide, or 5 wt % including 6 mol of ethylene oxide), polyoxyethylene nonylphenol ether phosphate (in an amount of 3 wt % including 11 mol of ethylene oxide, 80 wt % including 10 mol of ethylene oxide, 5 wt % including 9 mol of ethylene oxide, 6 wt % including 7 mol of ethylene oxide, or 6 wt % including 6 mol of ethylene oxide), polyoxyethylene nonylphenol ether phosphate (in an amount of 3 wt % including 13 mol of ethylene oxide, 80 wt % including 12 mol of ethylene oxide, 8 wt % including 11 mol of ethylene oxide, 3 wt % including 9 mol of ethylene oxide, or 6 wt % including 4 mol of ethylene oxide), polyoxyethylene nonylphenol ether phosphate (in an amount of 3 wt % including 17 mol of ethylene oxide, 79 wt % including 16 mol of ethylene oxide, 10 wt % including 15 mol of ethylene oxide %, 4 wt % including 14 mol of ethylene oxide, or 4 wt % including 13 mol of ethylene oxide), polyoxyethylene nonylphenol ether phosphate (in an amount of 5 wt % including 21 mol of ethylene oxide, 78 wt % including 20 mol of ethylene oxide, 7 wt % including 19 mol of ethylene oxide, 6 wt % including 18 mol of ethylene oxide, or 4 wt % including 17 mol of ethylene oxide), and Zelec UN™.

By cast polymerizing the polymerizable composition, a high-quality optical material having superior color and thermal stability and less time-dependent change, and being colorless and transparent may be obtained. The cast polymerization is carried out by injecting the polymerizable composition between a forming mold, a shape of which is maintained using a gasket, tape, or the like. In this regard, according to properties required for the obtained optical material or as needed, defoaming treatment under reduced pressure, or filtration treatment by addition or reduction of pressure may be preferred. Since polymerization conditions greatly vary according to polymerizable compositions, catalyst types, the amount of the catalyst, mold shapes, and the like, the conditions are not specifically limited. However, the polymerization is carried out for 1 to 50 hours at approximately −50 to 110° C. In some cases, curing is preferably performed for 1 to 48 hours while maintaining a temperature of 10 to 110° C. or slowly increasing temperature. As needed, the optical material obtained by curing may be annealed. The annealing may be generally carried out at 50 to 130° C., preferably 90 to 120° C.

In addition, during polymerization, a variety of additives such as a chain extender, a cross linking agent, a light stabilizer, an ultraviolet absorbent, an antioxidant, an anti-coloring agent, an oil-soluble dye, a filler, an adhesion improver, and the like may be added according to a desired purpose using publicly known molding methods. In particular, the catalyst plays an important role. As the catalyst, epoxy based curing agents are mainly used. However, since strong amines cause intense isocyanate reaction, the strong amines must be carefully handled. In the present invention, acid salts of amines, phosphonium salts, tertiary amines not having phosphines and electron attraction groups, Lewis acids, radical initiators, and the like are mainly used. One of ordinary skill in the art may determine a type and amount of a suitable catalyst as needed.

The polymerizable composition may be obtained as a variety of optical materials by changing a mold in a cast polymerization process. The obtained optical material may be used as an optical material of eyeglass lenses, camera lenses, light emitting diodes (LEDs), and the like, in a variety of use. In particular, the polythiourethane resin is suitable for an optical material of eyeglass lenses, camera lenses, light emitting diodes, and the like, or an optical device.

As needed, one surface or both surfaces of a lens composed of the optical material of the present invention may be coated with a coating layer. The coating layer may, for example, be a primer layer, a hard coat layer, an anti-reflective layer, an anti-fogging coating layer, an anti-fouling layer, a water-repellent layer, or the like. These coating layers may be coated alone or by layering a plurality of coating layers. When both surfaces are coated with coating layers, the coating layers may be the same or different.

EXAMPLE

Now, the present invention will be described in more detail with reference to the accompanying drawings. These examples are provided for illustrative purposes only and should not be construed as limiting the scope and spirit of the present invention.

Test and Evaluation Methods

A water content, resin color, thermal stability, and time-dependent change of polymerizable compositions were measured as follows.

Refractive index: a DR-M4 model available from Atago was used.

Water content: automatic moisture measurement was performed with Karl Fischer's solution, using a moisture meter available from Metrohm, equipped with a moisture vaporizer, 860KF thermoprep.

Resin color: ColorQuest XE available from Hunterlab was used as APHA and a plastic lens was directly inserted thereinto for measurement. Concentrations were datalized using a standard solution prepared by dissolving platinum and cobalt reagents and APHA values obtained by comparing a stored program and samples were used as measured values. Color is satisfactory with decreasing measurement value.

Thermal stability: cured optical lenses were maintained at 100° C. for 10 hours and color change was measured. When an APHA value was changed to less than 2, it was represented by "⊚". When an APHA value was changed to 2 or more and less than 4, it was represented by "○". When an APHA value was changed to 4 or more, it was represented by "x". ColorQuest XE available from Hunterlab was used as APHA and a plastic lens was directly inserted thereinto for measurement. Concentrations were datalized using a standard solution prepared by dissolving platinum and cobalt reagents and APHA values obtained by comparing a stored program and samples were used as measured values.

Time-dependent change: APHA values of lenses stored for 3 months and lenses before storing, which were obtained by curing an optical lens resin composition, were measured. When a difference value, Δ, of the measured APHA values was less than 2, it was represented by "⊚". When the difference value was 2 or more and less than 4, it was represented by "○". When the difference value was 4 or more, it was represented by "x".

Preparation of Polythioepoxy Compound

Each of bis(2,3-epithiopropyl)sulfide (BEPS) and bis(2,3-epithiopropyl)disulfide (BEPDS) was synthesized and then a water content thereof was reduced under reduced pressure. Subsequently, water contents were measured and then water was added such that water contents summarized in Table 1 are accomplished. Subsequently, each polythioepoxy compound was stored at a condition and in a period summarized in Table 1. Using the stored polythioepoxy compounds, eyeglass lenses were manufactured as described in examples below.

Example 1

89 g of bis(2,3-epithiopropyl)sulfide (BEPS), 5 g of isophorone diisocyanate, 6 g of bis(2-mercaptoethyl)sulfide, 0.15 g of 8-polyoxyethylene nonyl phenol ether phosphate (8-PENPP) (in amount of 3 wt % including 9 mol of ethyleneoxide, in amount of 80 wt % including 8 mol of ethyleneoxide, in amount of 5 wt % including 9 mol of ethyleneoxide, in amount of 6 wt % including 7 mol of ethyleneoxide, in amount of 6 wt % including 6 mol of ethyleneoxide), which is acidic phosphoric ester, as a mold release agent, 0.2 g of tetrabutylphosphonium bromide, 0.1 g of triphenylphosphine, an organic dye HTAQ (20 ppm) and PRD (10 ppm), and 1.5 g of HOPBT which is an ultraviolet ray absorbent, which are stored for 30 days under a condition of Table 1 below, were mixed at 20° C. to prepare a homogenous solution. The resultant mixed solution was defoamed at 400 Pa for 1 hour. Subsequently, the solution was filtered with a 1 μm PTFE filter and then injected into a molded case composed of a glass mold and tape. The molded case was inserted into a polymerization oven and was polymerized by elevating temperature from 25° C. to 100° C. through 21 hours. After terminating the polymerization, the molded case was taken out of the oven. A lens was obtained by releasing from the molded case. The obtained resin was additionally annealed at 100° C. for 4 hours. Properties of a resultant lens were measured and summarized in Table 1 below.

Examples 2 to 10

Each of compositions and lenses was prepared in the same manner as in Example 1, except that a polythioepoxy compound stored for 30 days under a condition of Table 1 below was used, and properties thereof were evaluated. Results are summarized in Table 1.

Comparative Examples 1 to 7

Each of compositions and lenses was prepared in the same manner as in Example 1, except that a polythioepoxy compound stored for 30 days under a condition of Table 1 below was used, and properties thereof were evaluated. Results are summarized in Table 1.

TABLE 1

| Classification | Storage condition and mixing amount of thioepoxy compound | | | | Refractive index (nE) | Resin color (APHA) | Thermal stability | Time-dependent change of lens (after 3 months) |
| --- | --- | --- | --- | --- | --- | --- | --- | --- |
| | Storage temperature(□) | Water content(ppm) | Storage days | Thioepoxy compound | | | | |
| Example 1 | −10 | 1000 | 30 days | 89 g of BEPS | 1.699 | 20 | ⊚ | ⊚ |
| Example 2 | −15 | 1200 | 30 days | 89 g of BEPS | 1.699 | 19 | ⊚ | ⊚ |
| Example 3 | −5 | 600 | 30 days | 89 g of BEPS | 1.699 | 23 | ○ | ○ |
| Example 4 | 0 | 800 | 30 days | 89 g of BEPS | 1.699 | 26 | ○ | ○ |
| Example 5 | 5 | 1500 | 30 days | 89 g of BEPS | 1.699 | 27 | ○ | ○ |
| Example 6 | 7 | 900 | 30 days | 89 g of BEPS | 1.699 | 28 | ○ | ○ |
| Example 7 | −15 | 800 | 30 days | 89 g of BEPS | 1.736 | 20 | ⊚ | ⊚ |

TABLE 1-continued

| Classification | Storage condition and mixing amount of thioepoxy compound | | | | Refractive index (nE) | Resin color (APHA) | Thermal stability | Time-dependent change of lens (after 3 months) |
| --- | --- | --- | --- | --- | --- | --- | --- | --- |
| | Storage temperature(□) | Water content(ppm) | Storage days | Thioepoxy compound | | | | |
| Example 8 | −5 | 2200 | 30 days | 89 g of BEPS | 1.699 | 24 | ○ | ○ |
| Example 9 | −30 | 1100 | 30 days | 89 g of BEPS | 1.699 | 18 | ◎ | ◎ |
| Example 10 | −50 | 1200 | 30 days | 89 g of BEPS | 1.699 | 18 | ◎ | ◎ |
| Comparative Example 1 | −20 | 3000 | 30 days | 89 g of BEPS | 1.699 | 35 | X | X |
| Comparative Example 2 | 0 | 3000 | 30 days | 89 g of BEPS | 1.699 | 60 | X | X |
| Comparative Example 3 | 15 | 1000 | 30 days | 89 g of BEPS | 1.699 | 45 | X | X |
| Comparative Example 4 | 15 | 400 | 30 days | 89 g of BEPS | 1.699 | 50 | X | X |
| Comparative Example 5 | 20 | 2800 | 30 days | 89 g of BEPS | 1.699 | 67 | X | X |
| Comparative Example 6 | −10 | 300 | 30 days | 89 g of BEPS | 1.699 | 47 | X | X |
| Comparative Example 7 | −10 | 3300 | 30 days | 89 g of BEPS | 1.699 | 43 | X | X |

ABBREVIATIONS

Monomers

BEPS: (bis(2,3-epithiopropyl)sulfide
BEPDS: bis(2,3-epithiopropyl)disulfide
HOPBT: 2-(2'-hydroxy-5'-t-octylphenyl)-2H-benzotriazole
HTQA: 1-hydroxy-4-(p-toluidine)anthraquinone
PRD: perinone dye

INDUSTRIAL APPLICABILITY

According to the present invention, a high-quality optical material having superior color and thermal stability, and less time-dependent change and being colorless and transparent may be prepared by inhibiting time-dependent change of a polythioepoxy compound during storage. The polythioepoxy based optical material prepared according to the present invention may be widely used in a variety of fields as a substitute for conventional optical materials. In particular, the thiourethane based optical material may be used in plastic eyeglass lenses, 3D polarizing lenses which are eyeglass lenses equipped with a polarizing film, camera lenses, and the like. In addition, the thiourethane based optical material may be used in a variety of optical products such as colorant filters, ultraviolet absorption filers, and the like.

The invention claimed is:

1. A method of storing a polythioepoxy compound for an optical material, the method comprising storing the polythioepoxy compound having a water content of 500 to 2,500 ppm at −78 to 10° C.
2. The method according to claim 1, wherein the polythioepoxy compound is stored at −50 to 0° C.
3. The method according to claim 2, wherein the water content is 600 to 1,500 ppm.
4. The method according to claim 1, wherein the polythioepoxy compound is stored for 3 years or less.
5. A method of preparing a polythioepoxy based optical material, the method comprising polymerizing a polymerizable composition comprising the polythioepoxy compound having a water content of 500 to 2,500 ppm, stored at −78 to 10° C.
6. The method according to claim 5, wherein the polymerizable composition further comprises a polyisocyanate compound.
7. The method according to claim 5, wherein the polymerizable composition further comprises a polythiol compound.
8. The method according to claim 5, wherein the polymerizable composition further comprises a polyisocyanate compound and a polythiol compound.
9. The method according to claim 5, wherein the polythioepoxy compound is at least one compound selected from the group consisting of bis(2,3-epithiopropyl)sulfide, bis(2,3-epithiopropyl)disulfide, 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, 2,5-bis(β-epithiopropylthiomethyl)-1,4-dithiane, 2,5-bis(β-epithiopropylthioethylthiomethyl)-1,4-dithiane, and 2-(2-β-epithiopropylthioethylthio)-1,3-bis(β-epithiopropylthio)propane.
10. A polythioepoxy based optical material prepared by the method according to claim 5.
11. An optical lens composed of the polythioepoxy based optical material according to claim 10.
12. The optical lens according to claim 11, wherein the optical lens is an eyeglass lens or a polarizing lens.

* * * * *